United States Patent [19]
Fullen et al.

[11] Patent Number: 5,736,656
[45] Date of Patent: Apr. 7, 1998

[54] APPARATUS AND METHOD FOR MEASURING THE MAGNITUDE AND DISTRIBUTION OF FORCES ON THE FOOT OF A QUADRUPED

[75] Inventors: Jeryl G. Fullen, Salina, Kans.; George R. Fullen, Littleton, Colo.

[73] Assignee: Fullen Systems, Inc., Littleton, Colo.

[21] Appl. No.: 652,279

[22] Filed: May 22, 1996

[51] Int. Cl.$^6$ ............................................. A61B 5/103
[52] U.S. Cl. ............................................. 73/865.4; 73/172
[58] Field of Search ........................... 73/865.4, 865.7, 73/172, 862.625, 862.626–862.629; 128/779

[56] References Cited

U.S. PATENT DOCUMENTS

| | | | |
|---|---|---|---|
| 546,700 | 9/1895 | Kean | 73/172 |
| 3,974,491 | 8/1976 | Sipe | 73/172 |
| 3,999,611 | 12/1976 | Bucalo | 168/4 |
| 4,189,004 | 2/1980 | Glass | 168/4 |
| 4,195,643 | 4/1980 | Pratt, Jr. | 128/779 |
| 4,233,845 | 11/1980 | Pratt, Jr. | 73/432 R |
| 4,421,119 | 12/1983 | Pratt, Jr. | 128/660 |
| 4,703,217 | 10/1987 | Ratzlaff et al. | 310/338 |
| 4,774,679 | 9/1988 | Carlin | 364/550 |
| 5,033,291 | 7/1991 | Podoloff et al. | 73/172 |
| 5,079,949 | 1/1992 | Tamori | 73/172 |
| 5,186,062 | 2/1993 | Roost | 73/865.4 |
| 5,323,650 | 6/1994 | Fullen et al. | 73/172 |
| 5,369,601 | 11/1994 | Tannenbaum | 364/558 |

FOREIGN PATENT DOCUMENTS

| | | |
|---|---|---|
| WO 89/01760 | 3/1989 | WIPO. |

OTHER PUBLICATIONS

Geddes, L. A., "Gaits of Horses: Marey Studies", Science vol. 151, Jan. 14, 1966.

*Primary Examiner*—Hezron E. Williams
*Assistant Examiner*—Nashimiya Ashraf
*Attorney, Agent, or Firm*—Sheridan Ross P.C.

[57] ABSTRACT

An improved apparatus and method are described for continuously measuring the timing and distribution of forces exerted against the entire surface of a quadruped's foot, thus providing a diagnostic tool to assist in measuring the ambulatory functions of an animal. The described force sensing device is lightweight, durable and worn by the animal in a manner which does not alter the natural movement of the quadruped. The device may be utilized without a shoe within an attached boot, or incorporated in a modified conventional horseshoe which fits over the hoof of the animal. The apparatus can further include a remote sensing and feedback function which allows the processing, storing, display and feedback of data indicative of the ambulatory functions of the animal at one or more remote locations.

14 Claims, 7 Drawing Sheets

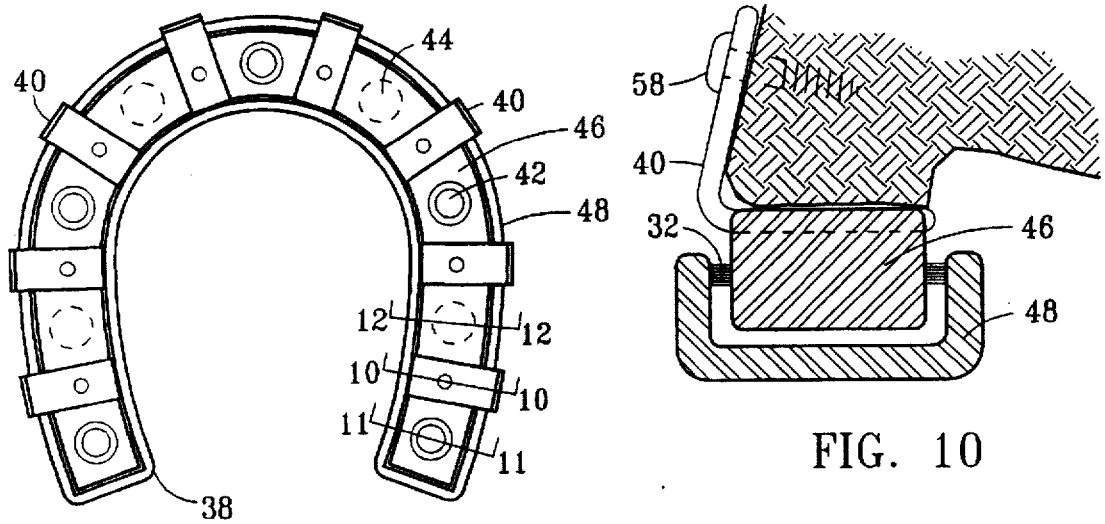
FIG. 8
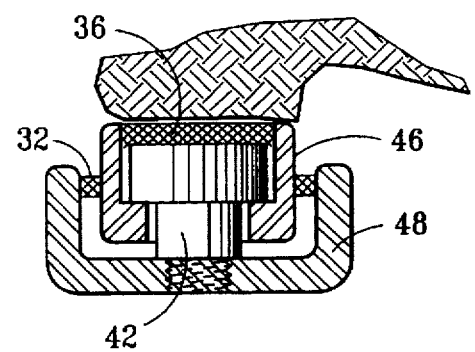
FIG. 10
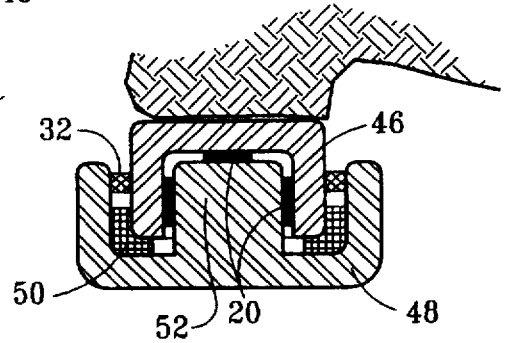
FIG. 11
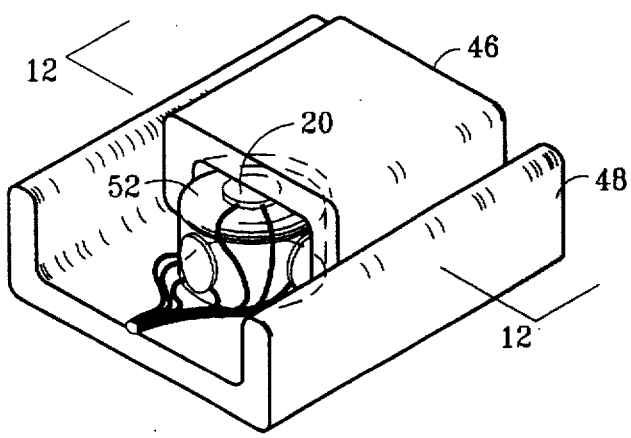
FIG. 9
FIG. 12

APPARATUS AND METHOD FOR MEASURING THE MAGNITUDE AND DISTRIBUTION OF FORCES ON THE FOOT OF A QUADRUPED

FIELD OF THE INVENTION

This invention relates to an apparatus and method for measuring the magnitude and distribution of forces applied against the foot of a quadruped without substantially altering the natural movement of the animal. More particularly, the apparatus is lightweight, worn by the quadruped, and can continuously measure the distribution and timing of forces exerted against the entire foot surface of an animal. By measuring and processing this data, various ambulatory functions of the quadruped can be measured, including gait, stride, and lameness. The apparatus and method may further include a wireless data transfer capability to provide continuous processing display and feedback of this data at one or more remote locations.

BACKGROUND OF THE INVENTION

Numerous attempts have been made in the field of veterinary medicine to measure the forces and timing of forces applied to the foot of a quadruped, and more particularly horses. This type of information is not only helpful for determining the stress applied to a foot, but may also be used as a diagnostic tool to analyze gait, stride, lameness and other symptoms which occur as a result of an animal's natural motion. Furthermore, this data is especially useful for analyzing racehorses, which are susceptible to injury and which may develop undesirable ambulatory mechanics if afflicted by foot and leg injuries which are undetected and untreated.

One type of apparatus used to measure forces exerted against the foot of a quadruped involves the positioning of a pressure plate, or platform, on the ground surface. The animal is then directed to walk or run over the surface and the force exerted by the foot of the animal is measured. However, these types of platforms are generally heavy, difficult to transport and are constructed of a hard surface which is generally avoided by a moving horse. Furthermore, these apparatus are only capable of measuring the total magnitude of force exerted against an entire foot surface, and not measure a distribution of forces applied against different portions of the foot.

Other apparatus have been developed which are worn on the foot of a quadruped, and thus avoid the transportation problems associated with the platforms previously mentioned. These devices include the use of accelerometers, resistive load cells, or force sensors with piezo transducers to measure the force applied against the foot of an animal. However, each of these devices only measures the total force exerted against the foot of an animal, and not the distribution or timing of those forces. More particularly, these devices have only been used to measure the force exerted against the rigid hoof of a quadruped, and not the force exerting against the remainder of the foot surface. Further, these devices have not been found to be durable and are difficult to calibrate as a result of the extreme pressures exerted by a horse or other large animal while running or jumping.

Finally, motion picture cameras and sound recording devices have been used to identify the timing of a quadruped's hoofs touching the ground. This information is then compiled and analyzed to measure gait and other ambulatory functions, but is limited in that it does not provide any information indicative of the force or distribution of forces applied against the foot of the animal. Additionally, these types of devices are burdensome, require a significant investment in expensive, cumbersome equipment, and generally cannot be utilized around an entire track or lengthy racing surface.

Thus, for the aforementioned reasons a significant need exists in the art for an apparatus and method for continuously measuring the distribution of forces applied against the foot of a quadruped. The device must be lightweight, capable of being worn by the animal without altering its natural movement, and durable enough to withstand the extreme foot pressures associated with large animals. Further, the device must be capable of measuring not only the distribution of forces against a hoof, or entire foot, but must be able to measure the timing of forces to process data indicative of gait, lameness and stride of the animal. Finally, it would be advantageous if the device would facilitate the processing and feedback of data indicative of force and ambulatory functions at a remote location. This capability would allow a trainer or rider of the quadruped to instantaneously evaluate data and respond accordingly for optimum ambulatory efficiency.

SUMMARY OF THE INVENTION

In accordance with the present invention a portable, lightweight force sensor worn on the foot or hoof of a quadruped and methods for using the same are provided. In one aspect of the invention, the apparatus comprises a plurality of individual force sensing elements which are positioned substantially coextensively to the bottom of the entire foot of a quadruped to measure the magnitude, distribution and timing of the forces applied against the foot. This plurality of force sensing elements is interconnected to make up a force sensing array which is generally positioned below the entire foot surface. The foot of the quadruped is generally comprised of a hard hoof and other soft tissue. The apparatus is comprised of certain durable, substantially non-destructible materials and is attached to the quadruped's foot in a manner which does not substantially alter the natural movement of the quadruped while walking, running or jumping. In this context, "non-destructible" means the material is capable of withstanding the forces exerted against a quadruped's foot for at least the time required to analyze the forces applied against the foot and other ambulatory functions. This device may include a flexible boot or other similar lightweight device which fits around the foot of the quadruped.

In accordance with another aspect of the invention, a signal receiving device is provided to receive signals from the force sensor array. The signal receiving device may additionally be used to either process the signals into useful information or to transmit the signals to a remote location. These signals can be indicative of the magnitude, distribution and timing of forces applied against the quadruped's foot and which are sensed by the plurality of individual force sensors. The signal receiving device is secured to the leg of the quadruped in a manner which does not substantially alter the quadruped's motion and can additionally process and generate information which is indicative of gait, stride, lameness and other ambulatory functions. To assure accurate force readings, the force sensor array and signal receiving device are calibrated using force loading machine and software which measures and compares actual and historically generated force measurement data.

In another aspect of the invention, a remote sensing device may be used to both receive and process information from the individual force sensing elements at a remote location. This remote sensing capability allows a trainer or a rider of the quadruped to evaluate, monitor and provide feedback to the quadruped based on the information received by the remote sensing device. The remote sensing device may further include a continuous output capability which continuously provides output related to the ambulatory performance of the quadruped at a remote location.

The apparatus can further include an interconnection device, such as a cable, for transferring one or more signals related to the magnitude, distribution and timing of the forces from the plurality of force sensing elements to the signal receiving device. The cable may be insulated or encased in a protective sheath to prevent damage to the cable.

In one particular aspect of the invention the individual force sensing elements include a pressure sensitive resistive material interposed between opposing electrodes. To provide cushioning and protection from foreign materials such as dust and rain an elastomeric material may additionally be positioned between the electrodes. Each of the electrodes are interconnected to incoming conductive leads and outgoing conductive leads. Furthermore, each of the individual force sensing elements may be interconnected with at least one other force sensing element with a conductive continuous lead material in a first direction and with a second continuous conductive lead material in a second direction. The intersection of the first and second continuous conductive lead materials in combination with the other individual force sensing elements defines a force sensing array.

In accordance with another embodiment of the invention, a method is provided for studying the ambulatory functions of a quadruped while the quadruped is moving in a substantially unrestricted manner. This method includes the steps of fitting on one or more feet of the quadruped an apparatus which measures the distribution of forces on the foot of the animal. The quadruped is then encouraged to move in either an assisted or non-assisted manner from a first location to a second location, while the forces applied against the foot of the quadruped are measured. The measured data are then transmitted to a sensing device located on either the quadruped, a rider, or at a remote location. This information is then transmitted to a remote analysis device or processed by a signal receiving device to compile and generate data which are indicative of the distribution and timing of force applied against the quadruped's hoof, along with other ambulatory functions. In one aspect of the described method, a rider positioned on the quadruped or a person at a remote location may receive information either visually or audibly which is indicative of the rate of the quadruped's foot falls, duration of foot contact to the ground surface, the relative timing of the foot falls, the total force and distribution applied against the foot gait, stride and other data which are useful to measure ambulatory functions of the quadruped. Furthermore, data received and collected by the remote sensing device can be stored for future reference and/or compared with derived standards for the individual quadruped.

In yet another embodiment of the invention, the apparatus may be used for measuring the magnitude and timing of forces applied against a hoof of a quadruped, and not the entire foot. This apparatus includes a substantially rigid shoe assembly shaped for attachment to the hoof. The shoe assembly is generally comprised of an inner shoe and an outer shoe, the inner shoe having a plurality of recessed openings to operatively receive individual force sensing elements between the inner shoe and the outer shoe. The inner shoe is attached to the hoof of the quadruped with nails or other means and the outer shoe is coupled to the inner shoe with screws or other fastening devices. Signals are received from the individual force sensing elements by a similar signal receiving means as previously described.

BRIEF DESCRIPTION OF THE DRAWINGS

FIG. 8 is a top plan view of a horse shoe assembly depicting the location of attachment clips, anchor screws and force sensor clusters.

FIG. 9 is a cutaway perspective view of a pressure sensor support module depicting the individual force sensors, conductive leads and relationship of the inner shoe and outer shoe.

FIG. 10 is a front sectional view of a cross section taken through line 10—10 in FIG. 8, showing the horseshoe outer shoe, inner shoe and attachment clip.

FIG. 11 is a cutaway sectional view taken along line 11—11 of FIG. 8.

FIG. 12 is a cutaway sectional view taken along line 12—12 of both FIG. 8 and FIG. 9.

DETAILED DESCRIPTION

Figure 1:
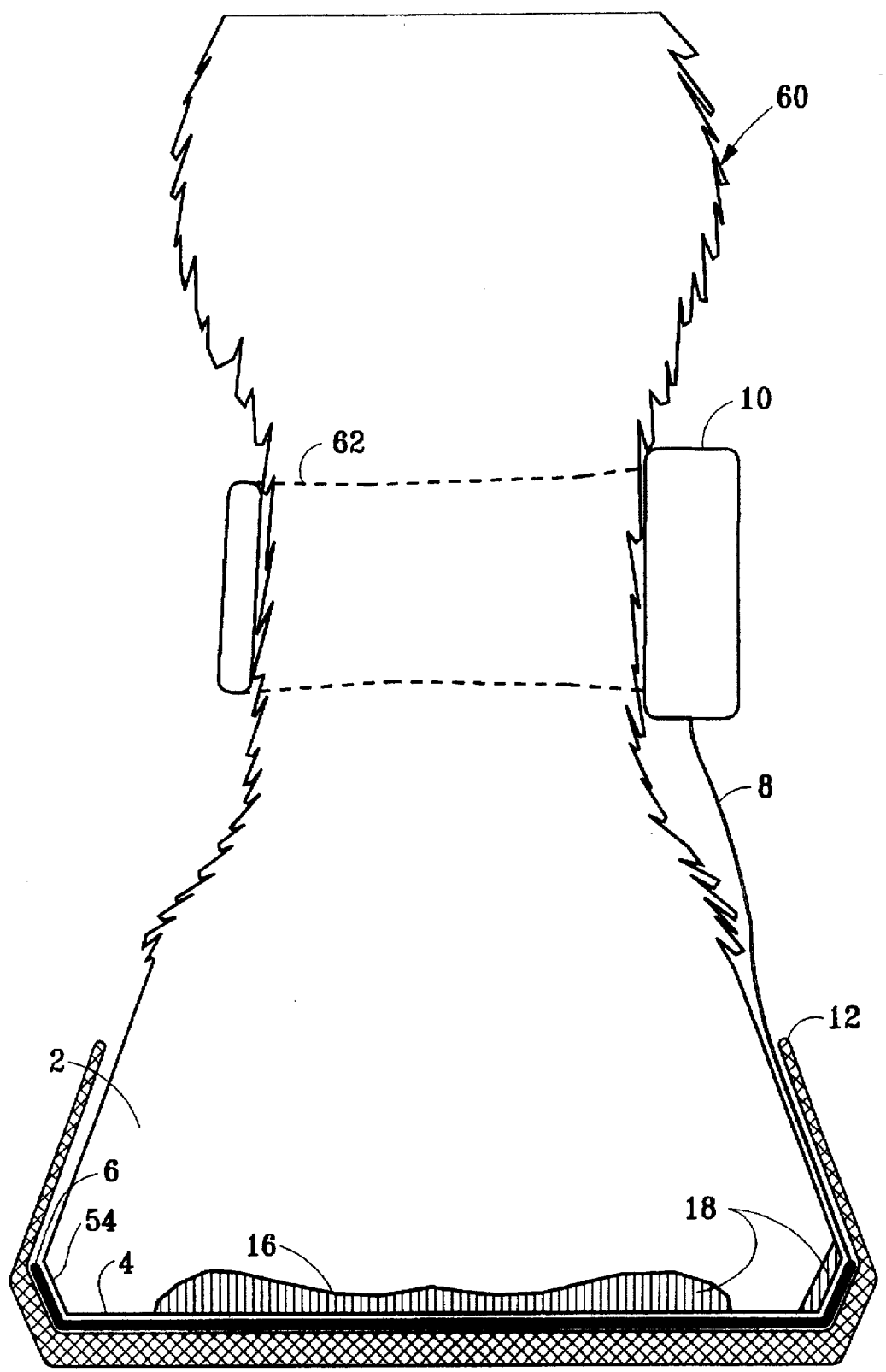
FIG. 1 is a front elevation view depicting the lower portion of a quadruped's leg and foot with a force sensor array positioned below the hoof with an attachment boot and interconnected to an electronics module.
Figure 3:
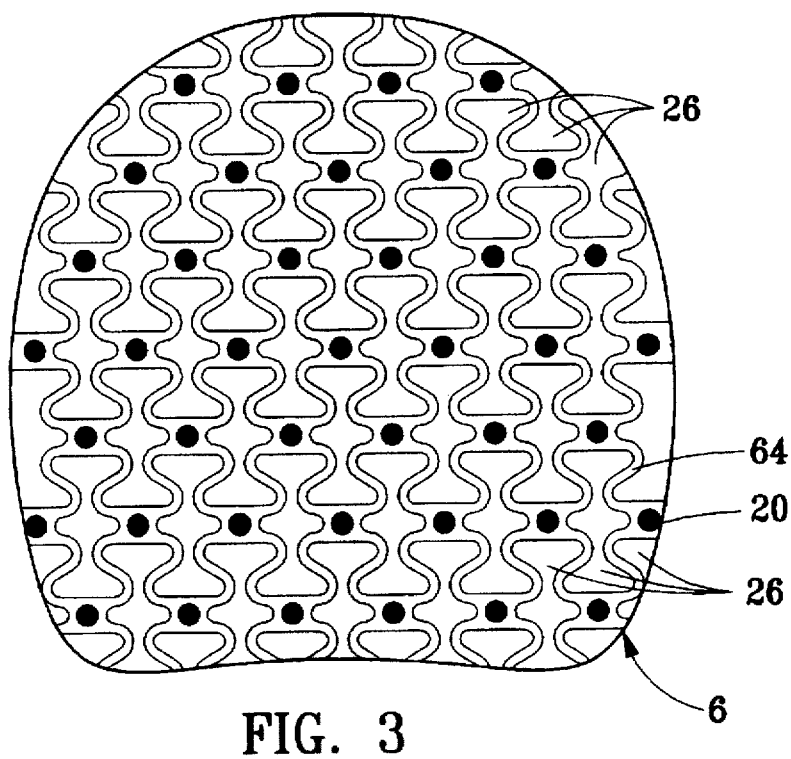
FIG. 3 is a plan view of a force sensor array comprised of a plurality of individual force sensors, conductive leads and cutout portions of a flexible substrate.

Referring now to the drawings, FIG. 1 depicts a front cutaway view of quadruped's lower leg 60, foot 2, and the attachment of one embodiment of a force sensor array and electronic module. As seen in FIG. 1, the foot of a quadruped is generally comprised of a hoof with a rigid bottom surface 4, a hoof insole 16, and a lateral hoof surface 54. In one embodiment of the present invention, a force sensor array 6 is positioned below the entire foot surface to cover the bottom surface of the hoof 4, the lateral surface of the hoof 54 and the hoof insole to measure the magnitude, distribution and timing of force applied vertically, horizontally, and tangentially against the animal's entire foot region. The force sensor array 6 is operably positioned below the animal's foot and is comprised of a plurality of individual force sensors 20 (FIG. 3). The force sensor array 6 is interconnected by means such as a conductive cable 8 to an electronics module 10 which is attached in a non-motion altering fashion to the animal's lower leg 60. As the animal walks, runs or gallops, the computer componentry within the electronics module 10 measures the distribution, timing and magnitude of forces applied against the animal's entire foot region.

Figure 2:
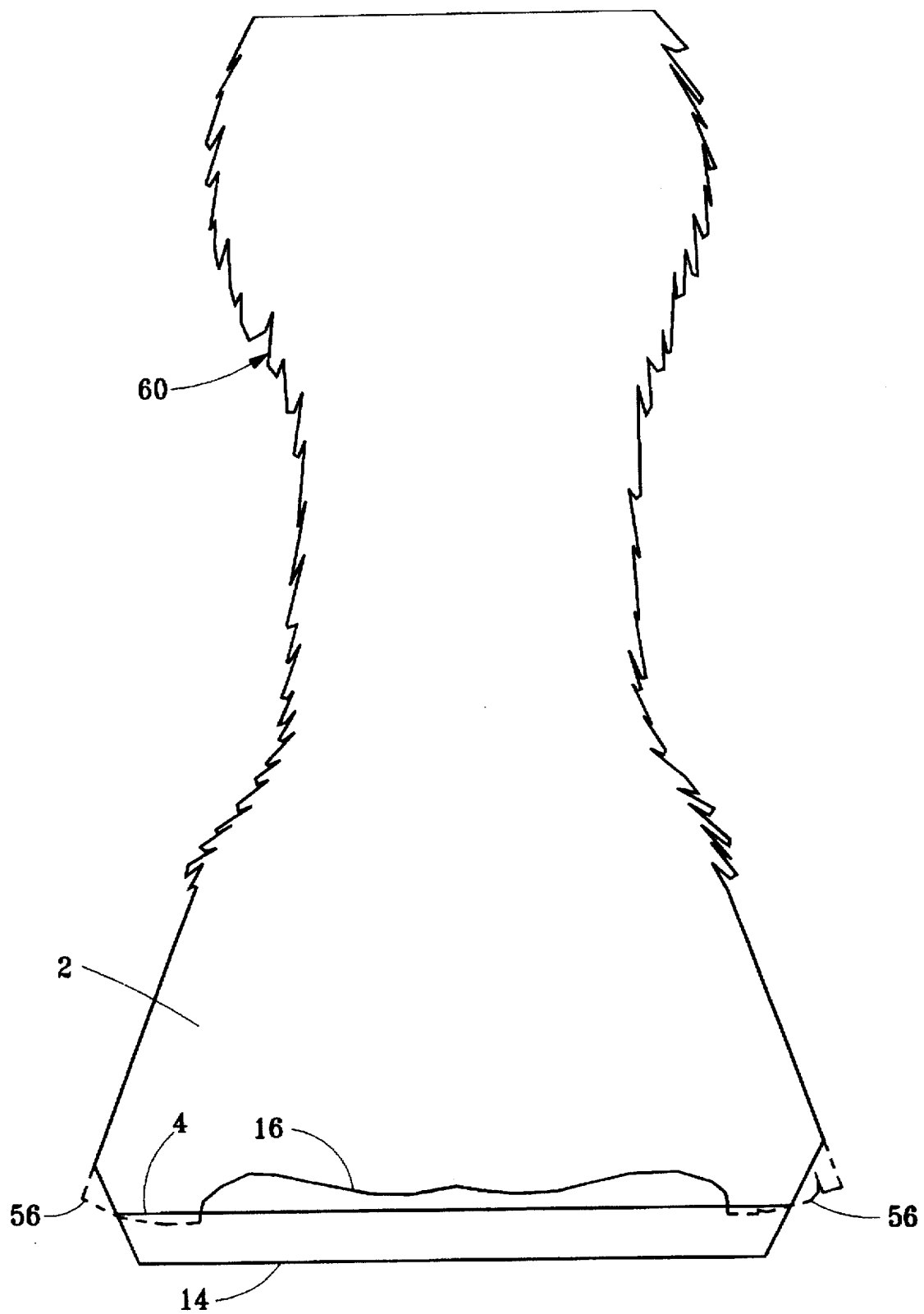
FIG. 2 is a front elevation view of a quadruped's hoof and lower leg with a template used for preparing the hoof surface positioned on the hoof.

In application, the bottom of the animal's foot 2 must generally be prepared (e.g., by a farrier) to accept the placement and positioning of the force sensor array 6 and device for holding the force sensor array 6 in an operable position. Without adequate preparation, the irregular bottom surface of the hoof 4 and insole 16 may create inaccurate force readings by the force sensor array 6. Referring now to FIG. 2, an animal's hoof 4 is shown with a template 14 positioned over the bottom surface of an animal's hoof 2 and hoof insole 16.

The template 14 is generally comprised of a rigid, durable material such as steel, iron, composite fiberglass or plastic and is positioned over the bottom hoof surface 4 of the animal. The template 14 is used as a guide to remove excess hoof material 56 with a file, rasp or other tool. The hoof is prepared to fit a particular model of template 14, which is sized to specifically fit an attachment boot 12. After the bottom and lateral hoof surfaces are filed and shaped, a fill material 18 is used to fill in the hoof insole 16 region of the animal's foot 2 to create a substantially flat surface. The fill material 18 may be comprised of an elastomer, plastic or other material which is pliable yet is generally incompressible when cured to allow an accurate force measurement when the pressure sensor array is positioned over the fill material 18. More preferably, the fill material is comprised of a very viscous or thixotropic two part silicone mold material.

Once the animal's hoof 4 is adequately prepared and the hoof insole 16 filled with the fill material 18, the force sensor array is placed on the bottom of the animal's hoof 4. Although the force sensor array 6 may be directly attached to the animal's hoof 4 with adhesives or other materials, it is preferred that the force sensor array 6 be interconnected to an attachment boot 12. More preferably, the force sensor array 6 is integrally interconnected within the attachment boot 12 to prevent any slipping or wrinkling under the animal's hoof 4 which may create an unreliable force reading. In a preferred embodiment, the force sensor array 6 is positioned around the outer perimeter of the animal's hoof 4 with the attachment boot 12 to allow the measurement of tangential and horizontal forces against the animal's hoof 4 as well as vertical forces applied against the bottom of the animal's hoof 4 and hoof insole 16.

The attachment boot 12 is comprised of a generally flexible material such as rubber, polyurethane or plastic and extends around the entire hoof region. The attachment boot 12 must be durable enough to prevent damage to the force sensor array 6, yet light and flexible enough to not alter the natural movement of the animal. More preferably, the attachment boot 12 is comprised of urethane. One particular product suitable for this type of application is the "EASY BOOT" manufactured by Easy Care, Inc. of Oro Valley, Ariz.

Figure 4:
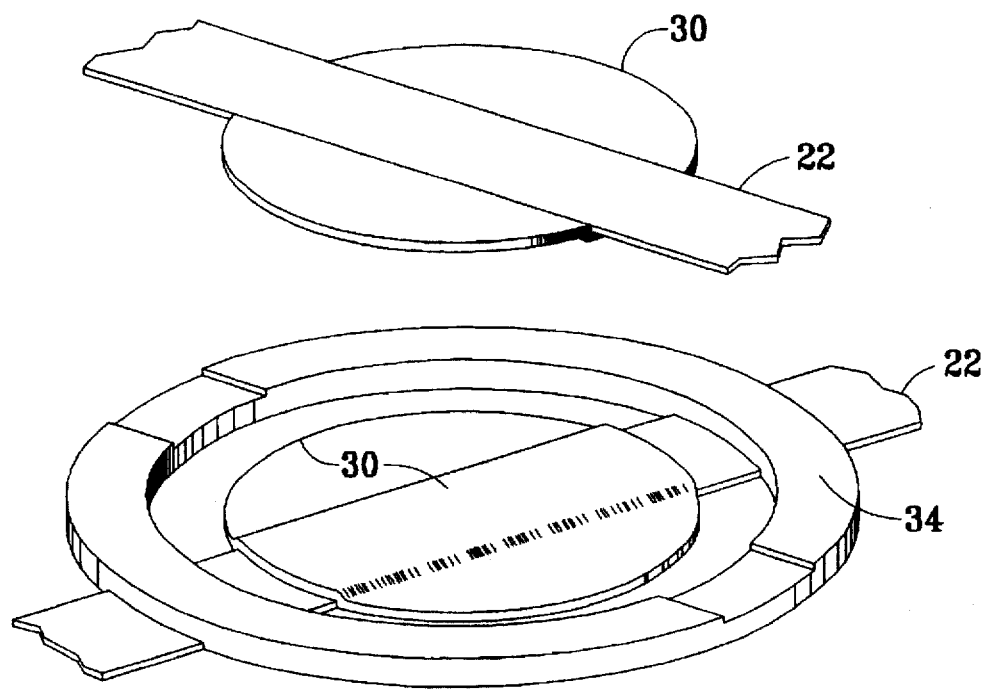
FIG. 4 is an exploded perspective view of an individual force sensor showing the relative positions of both input and output interconnecting conductive leads and the force sensitive resistive material.

Referring now to FIG. 3, in one embodiment of the present invention a force sensor array 6 is constructed with a plurality of individual force sensors 20 interconnected with conductive interconnection film 22 (FIG. 4). The interconnection film 22 is generally an extremely thin conductive material comprised of silver polymer. More preferably, the interconnection film 22 is a conductive screen printable material used in the membrane switch industry. The conductive leads 24 or interconnection film 22 is positioned on a substrate material such as polyester to provide a support surface for the individual force sensors 20 and interconnection film 22. To provide flexibility and wrinkle resistance to the force sensor array 6, a plurality of individual cutout portions 26 may be prepared in the substrate material. These individual cutout portions 26 may have a variety of shapes such as triangular, rectangular, hexagonal or oblong. More preferably, the individual cutout portions 26 are hourglass in shape.

Referring now to FIG. 4, an exploded perspective view of a typical individual force sensor 20 is shown. Generally, each individual force sensor 20 is constructed of opposing conductive interconnection film 22 having a pressure sensitive resistive material 30 positioned therebetween. The intersection of the conductive interconnection films 22 act as an electrode which measures the increase or decrease in resistivity and hence conductivity in the pressure sensitive resistive material. The interconnection film 22 may be made of copper or any other suitable conductive material. More preferably the interconnection film 22 is made of silver polymer. Generally, each of the force sensors 20 are about ⅛ inches in diameter and no greater than 0.01 inches in thickness, although other dimensions may be suitable.

Positioned between each of the individual opposing conductive electrodes is a pressure sensitive resistive material 30 and an adhesive ring 34. The pressure sensitive resistive material 30 is generally comprised of a material such as carbon filled polymer. The material must be pressure sensitive for accurate force readings, yet resilient and durable enough for repeatability and to withstand the significant forces applied against the hoofs of a large quadruped such as a horse. One such material, known as "Choflex" is manufactured by Chomerics in Woburn, Mass.

An adhesive glue ring 34 is generally positioned between the electrodes 22 and provides support and protection to the pressure sensitive resistive material 30 as seen in FIG. 4. In a preferred embodiment the adhesive glue ring 34 completely surrounds the perimeter of the pressure sensitive resistive material 30. The glue ring is a non-conductive adhesive bonding material. More preferably, the glue ring is an ultraviolet curable adhesive which does not outgas during the curing of the glue. The glue ring 34 has within its perimeter a pressure sensitive resistive material 30 which may additionally be printed onto the substrate material. On opposing surfaces of the glue ring are incoming and outgoing conductive leads 22. The conductive film is preferably silver polymer, although other commonly known conductive materials may be used. In practice, the glue ring 34, pressure sensitive resistive material 30 and interconnection film 22 may all be printed onto a substrate in a predetermined fashion to reduce the manufacturing costs associated with manually preparing the force sensor array 6. Furthermore, the adhesive glue ring 34 serves to form a more rigid sensor by resisting shear forces between the plastic substrates for the components shown in FIG. 4. The plastic substrate is not shown in FIG. 4.

Figure 5:
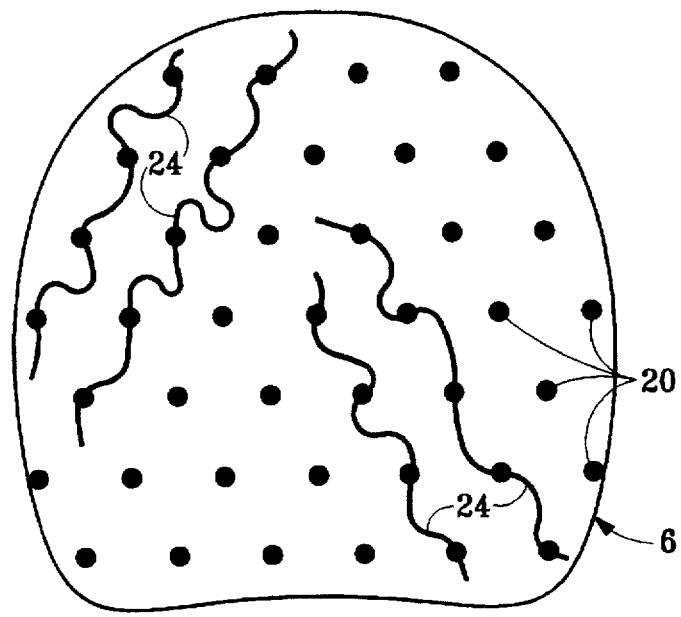
FIG. 5 is a plan view of an alternate force sensor comprised of a plurality of individual force sensors and interconnecting electrically conductive insulated leads all embedded in a supporting substrate structure.

Referring now to FIG. 5, an alternate embodiment of the present invention is shown which utilizes a force sensor array 6 comprised of a plurality of individual force sensors 20 interconnected with individual conductive leads 24. The conductive leads 24 are very fine and have multiple strands for flexibility. The force sensors 20 and conductive leads 24 are surrounded and supported by a polymer sheet (not shown). This device has the advantage of being more wrinkle resistant to prevent inaccurate pressure readings.

Figure 6:
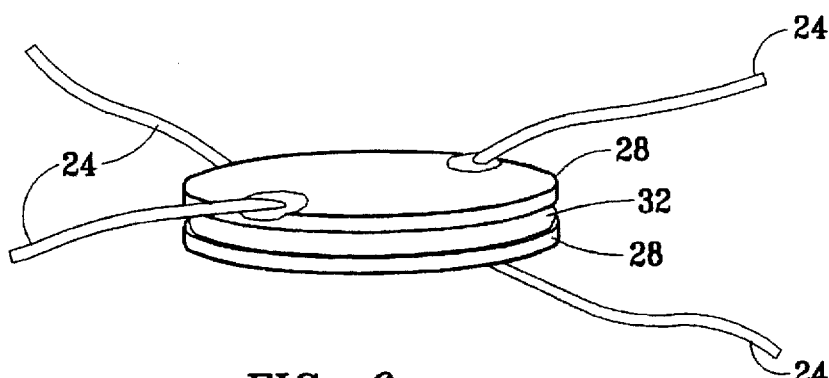
FIG. 6 is a front perspective view of an individual force sensor for use with the force sensor array of FIG. 5 and showing both input and output interconnecting conductive leads and opposing electrodes.

Referring now to FIG. 6, a perspective view of an alternate embodiment of individual force sensor 20 is shown. Generally, this embodiment of force sensor 20 comprises opposing metal electrodes 28 which are generally about ⅛ inch in diameter and no greater than ¹⁄₁₀₀ inch in thickness, although other dimensions, both smaller or larger may be appropriate depending on the application.

Figure 7:
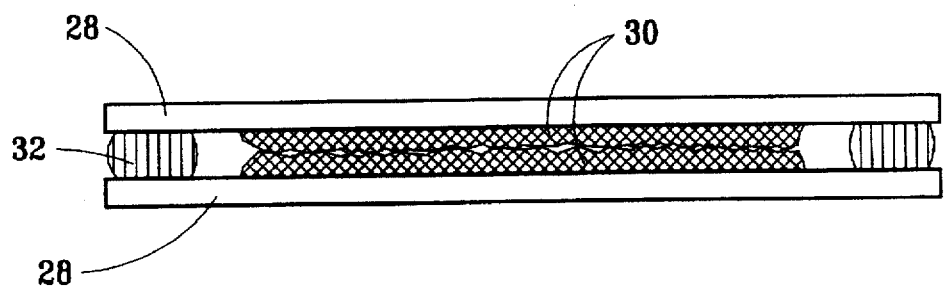
FIG. 7 is a sectional view of the individual force sensor of FIG. 6 and depicting internal components.

Referring now to FIG. 7, a sectional view of the individual force sensor 20 is shown in FIG. 6. Positioned between each of the individual opposing metal electrodes is a pressure sensitive resistive material 30 and an elastomer seal 32. The pressure sensitive resistive material 30 is generally comprised of materials which have a volume resistance of about one megohm per centimeter and are sufficiently elastic or pliable to cause added contact area and progressively less electrical resistance as the metal electrodes 28 are subjected to increased pressure. In operation current flows from one conductive lead 24 through one of the electrodes 28 which comprises a portion of each individual force sensor 20. Concurrently, current flows through another individual conductive lead 24 which flows into and out of the opposing electrode 28. One electrode 28 has a positive charge while the opposing electrode has a negative charge. As pressure is applied to the individual force sensor 20, the pressure sensitive resistant material 30 is compressed and the conductivity between the opposing electrodes 28 is increased and subsequently measured by, or transmitted from, the electronics module 10.

The elastomer seal 32 is generally positioned between the metal electrodes 28 and provides support and protection to the pressure sensitive resistive material 30 as seen in FIG. 7. In a preferred embodiment the elastomer seal 32 completely surrounds the perimeter of the pressure sensitive resistive material 30. The elastomer seal is generally comprised of a resilient plastic or polymer which completely entraps gas inside the sensor and also provides an impermeable seal to prevent the incursion of contaminants such as dirt or water which could damage or otherwise give inaccurate pressure readings. Furthermore, the elastomer seal provides a cushioning effect to help prevent damage to the pressure sensitive resistive material 30 as the metal electrodes are pushed towards one another.

In yet another embodiment of the present invention, an apparatus for measuring the distribution, timing and magnitude of forces applied against a quadruped's hoof wearing a conventional type of horseshoe is described. This particular embodiment may be seen in FIGS. 8–12. In general, a horseshoe assembly 38 is provided which comprises an outer shoe 48, an inner shoe 46, an attachment clip 40, a plurality of anchor screws 42 and a plurality of pressure sensor nodules 52. Each of the pressure sensor nodules 52 includes a plurality of individual force sensors 20 to measure the distribution, magnitude and timing of vertical, horizontal and tangential forces applied against the horseshoe assembly 38.

Referring to FIG. 8, a top plan view is shown depicting the top of the horseshoe assembly 38. The horseshoe assembly generally includes a plurality of attaching clips 40 which attaches the inner shoe 46 to the hoof of a quadruped. The inner shoe is generally comprised of a rigid, hard surfaced material such as steel, although hard plastics or other materials may be used. Preferably, the inner shoe 46 is comprised of stainless steel. The attachment clips 40 are interconnected to the inner shoe 46 and are bendable to conform to the shape of the animal's hoof. Additionally, an attachment screw 58 may be incorporated into the attachment clip 40 to further secure the attachment clip into the animal's hoof.

The outer shoe 48 is interconnected to the inner shoe 46 with one or more anchor screws 42. Preferably, a minimum of 3 anchor screws 42 are implemented, and more preferably 5 anchor screws 42 are used. The anchor screws 42 are screwed into threaded couplings in the outer shoe 48, and may be sealed with an anchor screw sealant 36 to help assure that the anchor screws do not become loose. Preferably, the inner shoe 46 and outer shoe 48 will be coupled together with the anchor screws 42 during the manufacturing process and before attachment to the hoof of a quadruped to assure proper tightness and quality control. The anchor screws 42 are generally comprised of steel, although other strong, preferably lightweight materials can be used.

The magnitude, distribution and timing of forces applied against the horseshoe assembly 38 are measured by a plurality of individual force sensors 20 which are positioned adjacent to or attached to a pressure sensor support nodule 52. The horseshoe assembly may include 2–3 force sensor support nodules 52, and more preferably 3–5. As shown in FIGS. 9 and 12, the force sensor support nodules are positioned between the inner shoe 46 and the outer shoe 48. Preferably, the force sensor support nodules are an integral part of the outer shoe 48 as shown in FIG. 12. The pressure sensor support nodule 52 may be square, rectangular, cylindrical or any other geometric shape which facilitates the positioning and attachment of the individual force sensors 20. Preferably, the pressure sensor nodule is cylindrical, which permits the attachment of at least 5 individual force sensors 20. This configuration allows one individual force sensor 20 on each opposing side of the pressure sensor nodule 52 and one individual force sensor 20 vertically positioned on the upper surface of the pressure sensor nodule and directly against the surface of the inner shoe 46. As previously discussed, each of the individual force sensors have an incoming and outgoing conductive lead 24 which transmits a signal from the individual force sensors 20 to the computer componentry in the electronic module 10.

Referring now to FIG. 12, which is a cross-section of FIG. 9 taken at lines 12—12, the relationship between the inner shoe 46, outer shoe 48, and individual force sensors 20 can be seen. In one embodiment, an elastomer support 50 and elastomer seal 32 is provided which is positioned between the inner shoe 46 and outer shoe 48. The elastomer support 50 is used to provide a cushion between the inner shoe 46 and outer shoe 48 and to prevent any direct contact between the inner shoe 46 and outer shoe 48. The elastomer support 50 material is generally comprised of a semi-flexible polymer material such as rubber or plastic. More preferably, the elastomer support 50 is comprised of silicone rubber.

An elastomer seal 32 may additionally be positioned between the inner shoe 46 and outer shoe 48 and is utilized primarily as a seal to prevent moisture, dust or other contaminants from contacting the individual force sensors 20, conductive lead 24, and to cushion any movement between the inner shoe 46 and the outer shoe 48. The elastomer seal is generally constructed of a flexible polymer, plastic or rubber, although any number of materials can be used as a sealant. Preferably the elastomer seal 32 is polyurethane.

In each of the aforementioned embodiments of the present invention, as force is applied by the hoof of a quadruped the individual force sensors 20 measure the applied force and send a signal through the conductive lead 24 and conductive cable 8 to the electrical componentry in the electronics module 10. The actual force is determined by measuring a change in the resistivity and hence conductivity of the pressure sensitive resistive material 30 of each individual force sensor 20 as pressure is applied. Thus, when more force is applied, there is less distance between the interconnection film 22 electrodes (FIG. 4) or electrodes 28 (FIG. 6) on either side of the pressure sensitive resistive material 30 and hence greater conductivity which is measured by the electronic componentry in the electronics module 10.

The componentry in the electronics module 10 is designed to receive signals from the individual force sensors 20. The electronics module must be small and light enough for attachment to the lower leg of the quadruped in such a way to assure that the animal is capable of walking or running in a substantially normal state. Preferably, the electronics module weighs no more than 6 ounces and is no greater in size than 2 inches by 4 inches. More preferably, the electronics module weighs approximately 3 ounces and is a dimension no greater than about 2 inches by 2 inches. The electronics module may be attached to the animal's lower leg with an attachment strap 62 or band. Preferably, the strap is made of elastic or polyester web belting with a VELCRO® type loop and hook attachment mechanism, although other types of lightweight attachment mechanisms may be utilized.

The electronic componentry in the electronics module 10 is designed to measure the magnitude and distribution of forces exerted against the force sensor array or force sensor support module 52. This is accomplished by measuring the aforementioned signals generated by each individual force sensor 20. By measuring the timing of these forces, the gait, stride, lameness and other ambulatory mechanics of a quadruped can be measured and used for diagnostic purposes and for optimization of treatment programs for various injuries. To assure accurate force and pressure readings, the individual force sensors and force sensor array can be properly calibrated. This is accomplished by utilizing a hydraulic or pneumatic pressure loading machine and a computer program which translates voltage values measured at any force sensor into actual force readings. The calibration is accomplished by positioning a force sensor array 6 into a hydraulic or pneumatic loading machine and applying numerous known forces to the force sensor array. As force is applied to the force sensor array, the relation of the actual force to the digital values received by the measurement equipment can be measured and coordinated. Successive readings and scannings thus form an iterative procedure which eventually generates a database of optimum calibration values. Furthermore, the computer software program may include a time based method to compensate for the natural hysteresis which occurs to the individual force sensors. This may be accomplished by reducing a predetermined force amount over time to neutralize the effects of material hysteresis.

Figure 13:
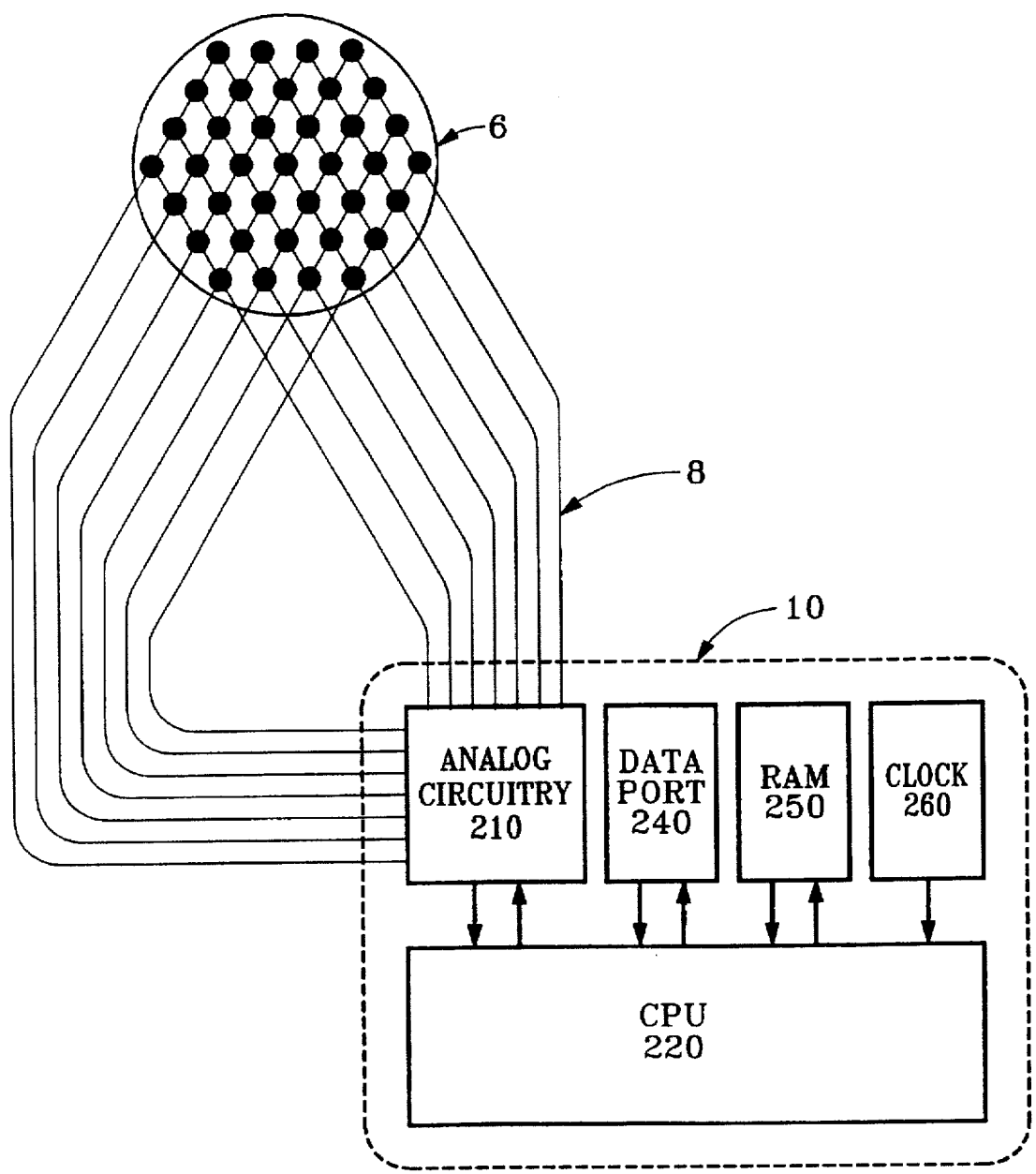
FIG. 13 is a block diagram showing the functional components of the force sensor array and electronic module and the general flow of data.

Referring now to FIG. 13, the electronics module contains analog circuitry 210 controlled by a central processing unit (CPU) 220. CPU 220 executes software routines stored in internal ROM memory during system boot and thereafter executes software programs as controlled by data in a random access memory (RAM) 250. An interface data port 240 is used to up-load data stored in RAM 250 to an external personal computer (PC) and to down-load operational data from a PC to RAM 250. A time of day and calendar clock 260 provides time and date information to CPU 220. In addition, a wireless data transmitter (not shown) may be included to interface the electronic circuit module 10 to external electronic equipment for the purpose of transferring data and other information between electronic circuit module 10 and the external electronic equipment.

Figure 14:
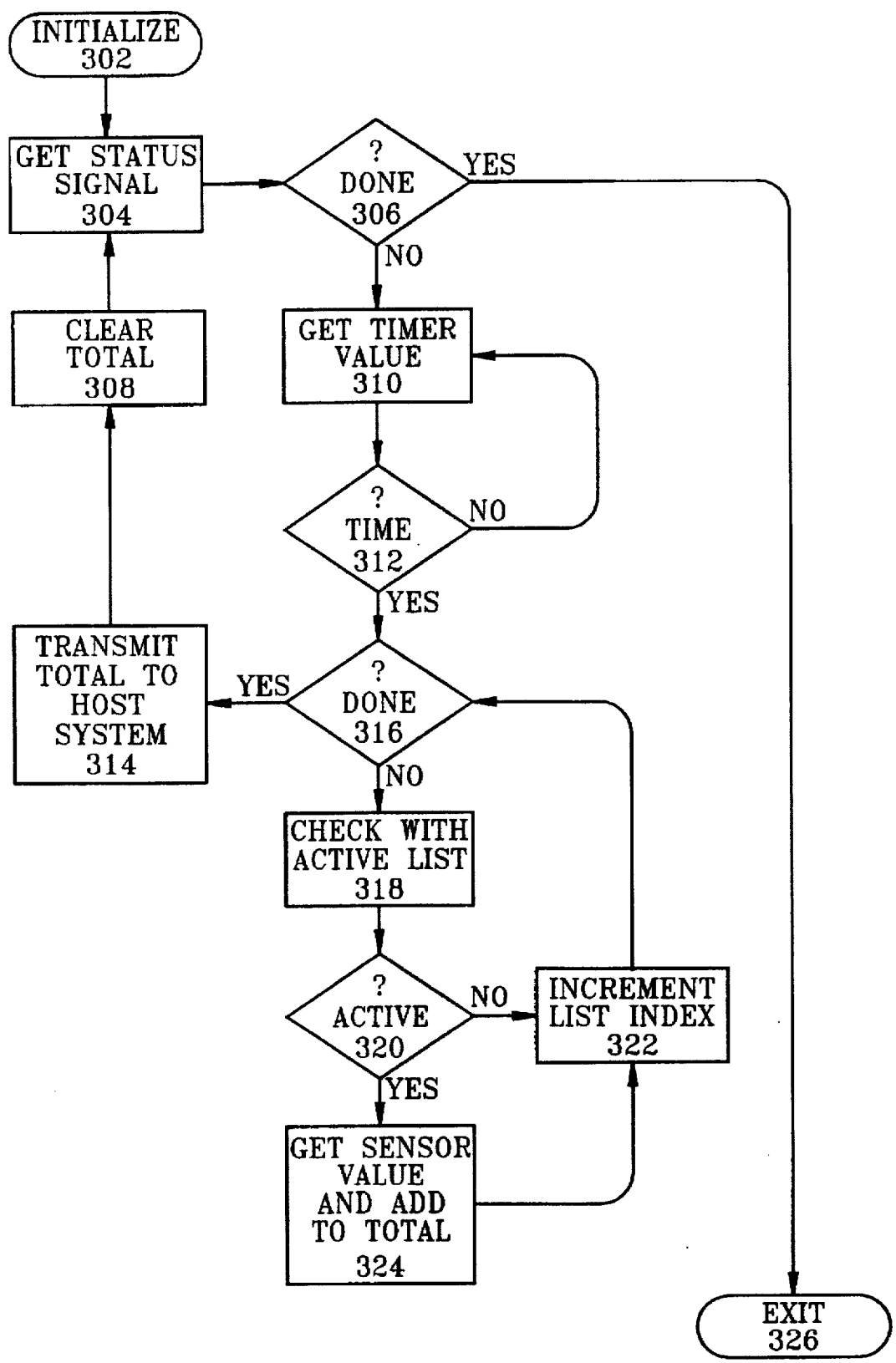
FIG. 14 is a flow chart of a routine performed by the circuitry within the electronic module.

Referring now to FIG. 14, there is shown a flowchart for a software program executed by CPU 220 contained within electronic circuit module 10 to facilitate operation of the foot force measurement system of the present invention. Initialization step 302 can be a conventional software initialization step involving setting memory areas to proper values, checking hardware configurations, etc. Step 304 reads control data generated by a data display computer under operator control. This data is tested by step 306, and if appropriate, entry into the force monitoring routine is started by transferring control to step 310. Otherwise, control is passed to step 326 to exit the routine. The force sensor array 100 can be scanned many times per second. The loop formed by steps 316–324 is executed as many times as there are sensor addresses within the array. However, not all possible addresses will be connected to actual sensors. Entry into the array scanning loop 316–324 is not done until it is time to do so as determined by the timing loop of steps 310 and 312. The effect of this timing loop is to suspend force measurements until a proper time is reached and thus control the time interval between measurements. Step 312 compares the value produced by step 310 with a desired value and transfers control to step 316 to start the scanning loop when these two values match. Step 316 tests for conditions which indicate completion of a scan of the force sensor array. Of course, this will not be the case on entry into this loop. Step 320 compares the two vector address unique to each iteration of the loop with a list of active sensors. If the present address is on the list, control is transferred to step 324. Step 324 uses the address information to analog circuitry elements to apply voltage to the selected sensor. The current through each of the sensors of force sensor array 6 is thus measured in a predetermined order and consequently the individual force sensors can be associated with data stored in RAM 250 by which the current flow through each sensor can be individually translated into calibrated force values. This data controls the charging time for a resistive/ capacitance circuit, is input data for numerical algorithms, and index data for a look-up table. The force value is accumulated for all iterations of this loop. Step 322 determines which address is to be checked next by step 316. When completion of the scan is detected by step 316, control is passed to step 314. Step 314 provides a data transfer link to other parts of the system. This is followed by resetting the total force value to zero in preparation for another scan of the sensor array before passing control back to step 304.

In another embodiment of the present invention a remote sensing means is utilized to receive and process data from the signal receiving device located on the leg of the quadruped. This remote sensing device may be located on the rider of the quadruped, on a saddle positioned on the animal, in the helmet of the rider or at a stationary location adjacent a race track or other running or walking surface. Generally, this system utilizes a primary computer and attached sensor apparatus, a wireless data transfer device consisting of a spread spectrum uplink and an FSK (frequency shift keying) downlink. This will include another data communications unit connected to a computer. Appropriate software can also be used.

In use, the hoof force measurement system described above is capable of measuring the instantaneous force on all of the individual force sensors within force sensor array 6 during a scan that takes place at regular, predetermined time intervals. The scan rate is fast enough to assure a multiplicity of scans for any hoof strike and thus capture any significant instantaneous force value. Consequently, a time-based plot of force on the entire foot or any part thereof may be produced for each foot strike. The force centroid or balance point of forces placed on a foot or portions of a foot may be computed for each scan of force sensor array 6 because the relative position of each of the individual sensors within force sensor array 6 is fixed and known. Therefore, a time-based two-coordinate plot of the path of the centroid may be produced for each hoof strike. Any force placed on the hoof in excess of that required to counteract the quadruped's weight may be assumed to be due to acceleration resulting from work done by that animal. This acceleration can be used to compute an instantaneous resultant velocity from which the mechanical power produced by the animal can be computed. Using these primary measurements and computations, information can be produced which is useful in a variety of circumstances including but not limited to those discussed below.

The present invention can be used in practice by veterinarians to identify and diagnose subtle limb problems in a quadruped and to custom tailor appropriate treatment regimes or weight altering systems for fractured limbs. Further, a trainer can use the present invention to monitor an animal's progress or development on an ongoing basis. Additionally, a trainer or farrier can use the system to confirm proper hoof preparation for shoeing as well as for modifying and custom fitting shoes depending on the application. Finally, jockeys or trainers can use the real time capability of the present invention during training or competitive events as an early warning system or as a pacing mechanism.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described herein above are further intended to explain best modes known of practicing the invention and to enable others skilled in the art to utilize the invention in such, or other embodiments with various modifications required by the particular application(s) or use(s) of the present invention. It is intended that the appended claims be construed to include alternative embodiments to the extend permitted by the prior art.

The following numbering of the components of the drawings are provided for clarity:

02 Horses Hoof
04 Bottom Surface of Hoof
06 Force Sensor Array
08 Conductive Cable
10 Electronics Module
12 Attachment Boot
14 Template
16 Hoof Insole
18 Fill Material
20 Individual Force Sensor
22 Interconnection Film
24 Individual Conductive Leads
26 Cutout Portions
28 Metal Electrodes
30 Pressure Sensitive Resistive Material
32 Elastomer Seal
34 Glue Ring
36 Anchor Screw Sealant -continued 38 Horse Show Assembly
40 Attachment Clip
42 Anchor Screws
44 Force Sensor Clusters
46 Inner Shoe
48 Outer Shoe
50 Elastomer Support
52 Pressure Sensor Support Nodule
54 Lateral Surface of Hoof
56 Excess Hoof Material
58 Attachment Screw
60 Lower Leg
62 Electronics Module Attachment Strap
64 Plastic substrate
210 Analog Circuitry
220 Central Processing Unit
240 Interface Data Port
250 Random Access Memory
260 Calendar Clock
302 Initialization Step
304 Status Signal Step
306 Testing Step
308 Clear Total Step
310 Timer Value Step
312 Value Comparison Step
314 Transmit Step
316 Completion Test Step
318 Active List Step
320 Comparison Step
322 Increment List Step
324 Sensor Value Step
326 Exit Step

What is claimed is:

1. An apparatus for measuring the magnitude, distribution and timing of forces exerted against a foot of a quadruped, comprising:

(a) a plurality of individual force sensing elements interconnected to a wrinkle resistant substrate having a plurality of individual cutouts and positioned substantially coextensive with the bottom of the entire foot of said quadruped to measure the magnitude, distribution and timing of forces applied against said foot, said foot comprising a hard hoof and other soft tissue;

(b) attachment means for holding said plurality of force sensing elements in an operable position below said foot of said quadruped, wherein said attachment means comprises a boot which fits substantially around the entire foot of the quadraped;

(c) signal receiving means for receiving signals from said plurality of individual force sensing elements which are indicative of the magnitude, distribution and timing of forces applied against said foot and sensed by said plurality of individual force sensing elements;

(d) securement means for holding said signal receiving means in a non-motion-altering position on a leg of said quadruped; and (e) interconnection means for transferring one or more signals related to the magnitude, distribution and timing of forces from said plurality of force sensing elements to said signal receiving means.

2. The apparatus of claim 1, wherein said individual force sensing elements are comprised of a pressure sensitive resistive material interposed between opposing electrodes, each of said electrodes interconnected to an incoming conductive lead and an outgoing conductive lead.

3. The apparatus of claim 2, wherein said individual force sensing elements further comprise a substantially elastomeric dielectric material interposed between said opposing electrodes.

4. The apparatus of claim 1, wherein said attachment means comprises a flexible boot which fits around substantially the entire foot of said quadruped.

5. The apparatus of claim 1, wherein said plurality of individual force sensing elements are interconnected to said attachment means in a manner which is substantially nondestructible when force is applied to said plurality of individual force sensing elements by the foot of said quadruped.

6. The apparatus of claim 1, wherein said securement means comprises a band interconnected to said signal receiving means, said band having a first end with interconnected loops and a second end with interconnected hooks.

7. The apparatus of claim 1, wherein said interconnection means comprises a plurality of conductive leads held together in a protective sheath.

8. The apparatus of claim 1, wherein each of said individual force sensing elements are interconnected with at least one other force sensing element in a first direction with a first continuous conductive lead material and in a second direction with a second continuous conductive lead material, wherein the intersection of said first and said second continuous conductive lead materials defines at least a portion of a force sensing array.

9. The apparatus of claim 1, wherein said wrinkle resistant substrate is stretchable in at least one direction.

10. The apparatus of claim 1, wherein said signal receiving means monitors, processes, stores or transmits to a remote location information which is indicative of ambulatory functions of said quadruped.

11. The apparatus of claim 1, further comprising remote sensing means for receiving and processing information received from said signal receiving means.

12. The apparatus of claim 11, wherein said remote sensing means further comprises output means which continuously provides output at a remote location of information indicative of the stride and gait of said quadruped determined from data received from said individual force sensing elements.

13. An apparatus for continuously measuring the magnitude, distribution and timing of forces on a quadruped's feet, including data which is indicative of the ambulatory functions of said quadruped, said apparatus comprising:

(a) a force sensor array shaped to cover substantially the entire bottom surface of each of the feet of said quadruped, said force sensor array comprising a plurality of individual force sensors interconnected to a flexible, wrinkle resistant substrate having a plurality of individual cutouts;

(b) a boot comprising a bottom section interconnected to flexible side walls for securing said boot to each of said feet of said quadruped, said bottom section comprising a ground contacting surface and foot contacting surface with said force sensor array positioned between said foot contacting surface and said ground contacting surface;

(c) signal receiving means for receiving, measuring, or transmitting data indicative of the distribution and timing of forces exerted on each foot of said quadruped;

(d) interconnection means for transferring one or more signals between said force sensor array to said signal receiving means;

(e) attachment means for attaching, in a non-motion-altering manner, said signal receiving means to a leg of said quadruped; and (f) remote data means for receiving monitoring and/or processing information received and generated from said signal receiving means at a remote location.

14. The apparatus of claim 13, wherein said substrate can substantially conform in shape to non-planar surfaces without wrinkling.

* * * * *